United States Patent
Michida et al.

(10) Patent No.: US 7,534,782 B2
(45) Date of Patent: May 19, 2009

(54) CRYSTAL OF 1-METHYLCARBAPENEM SOLVATE

(75) Inventors: Makoto Michida, Tokyo (JP); Yuki Nagao, Kanagawa (JP)

(73) Assignee: Sankyo Company, Limited, Tokyo (JP)

( * ) Notice: Subject to any disclaimer, the term of this patent is extended or adjusted under 35 U.S.C. 154(b) by 369 days.

(21) Appl. No.: 11/352,825

(22) Filed: Feb. 13, 2006

(65) Prior Publication Data

US 2006/0189592 A1 Aug. 24, 2006

Related U.S. Application Data

(63) Continuation-in-part of application No. PCT/JP2004/012604, filed on Aug. 25, 2004.

(30) Foreign Application Priority Data

Aug. 25, 2003 (JP) ............... 2003-299677

(51) Int. Cl.
C07D 477/20 (2006.01)
A61K 31/407 (2006.01)
A61P 31/04 (2006.01)

(52) U.S. Cl. ............... 514/210.13; 540/350

(58) Field of Classification Search ........... 540/350; 514/210.13
See application file for complete search history.

(56) References Cited

U.S. PATENT DOCUMENTS

| | | | |
|---|---|---|---|
| 6,090,802 A | 7/2000 | Kawamoto et al. | |
| 6,924,279 B2 | 8/2005 | Kawamoto et al. | |
| 7,041,660 B2 * | 5/2006 | Kawamoto et al. | 514/210.13 |
| 2002/0128254 A1 | 9/2002 | Kawamoto et al. | |
| 2003/0232803 A1 | 12/2003 | Kawamoto et al. | |
| 2004/0132668 A1 | 7/2004 | Kawamoto et al. | |
| 2008/0227768 A1 * | 9/2008 | Michida et al. | 514/210.13 |

FOREIGN PATENT DOCUMENTS

| | | | |
|---|---|---|---|
| JP | 10-204086 A | | 8/1998 |
| JP | 2965922 B2 | | 8/1998 |
| JP | 11-071277 A | | 3/1999 |
| JP | 2955276 B2 | | 3/1999 |
| JP | 2001-072681 A | | 3/2001 |
| JP | 2001114759 A | * | 4/2001 |
| JP | 2002-161034 A | | 6/2002 |
| WO | WO 97/23483 A1 | | 7/1997 |

OTHER PUBLICATIONS

U.S. Appl. No. 11/901,942, filed Sep. 19, 2007, Art Unit 1614, Confirmation No. 7924.
U.S. Appl. No. 11/919,932, filed Nov. 15, 2007, Art Unit 1614, Confirmation No. 8345.

* cited by examiner

*Primary Examiner*—Mark L Berch
(74) *Attorney, Agent, or Firm*—Frishauf, Holtz, Goodman & Chick, P.C.

(57) ABSTRACT

A 1-methylcarbapenem compound ethanolate of the formula (I-1) in the crystalline form that shows main peaks at interplanar spacings d=7.60, 6.69, 6.33, 6.14, 5.15, 4.58 and 4.48 in the X-ray powder diffraction pattern obtained with Cu $K_\alpha$ irradiation

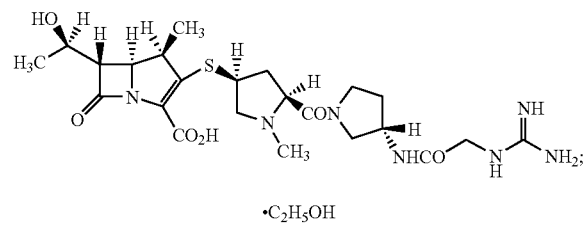

(I-1)

and a 1-methylcarbapenem compound tetrahydrate of the formula (I-2) in the crystalline form that shows main peaks at interplanar spacings d=11.68, 8.79, 7.53, 6.57, 5.58, 5.37, 3.99 and 3.09 in the X-ray powder diffraction pattern obtained with Cu $K_\alpha$ irradiation

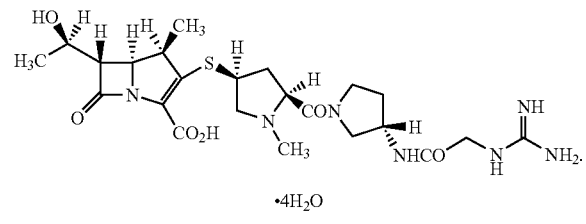

(I-2)

These compounds are useful for treating or preventing bacterial infections.

23 Claims, 2 Drawing Sheets

CRYSTAL OF 1-METHYLCARBAPENEM SOLVATE

CROSS-REFERENCE TO RELATED APPLICATION

This application is a continuation-in-part application of International application PCT/JP2004/012604 filed Aug. 25, 2004, the entire contents of which are incorporated by reference herein.

BACKGROUND OF THE INVENTION

This invention is directed to crystalline forms of 1-methylcarbapenem compounds that exhibit excellent antibiotic activity against various bacterial strains and are stable enough to keep for a long time, and have high producability or handling ease. This invention is directed to medicaments containing a crystalline form of the present invention as an active ingredient (and particularly pharmaceutical compositions for the prevention or treatment of bacterial infections). This invention is directed to the use of a crystalline form of the present invention for the manufacture of a medicament for the prevention or treatment of bacterial infections. This invention is directed to methods for preventing or treating bacterial infections which comprise administering an effective amount of a crystalline form of the present invention to a warm-blooded animal in need of such prevention or treatment. Further this invention is directed to processes for the preparation of crystalline forms of the present invention.

BACKGROUND ART

The 1-methylcarbapenem compound of the following formula is disclosed in Japanese Patent Application Publications (Kokai) Hei-10-204086 and Hei-11-071277, and U.S. Pat. No. 6,090,802.

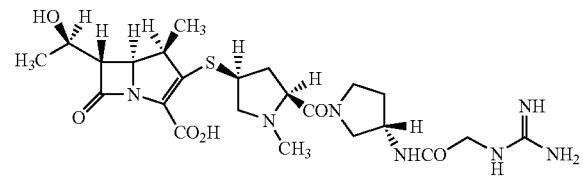

This compound (I) exhibits excellent antibiotic activity not only against Gram-negative bacterial strains but also against Gram-positive bacterial strains and can be expected to become a useful antibiotic agent.

Specific crystalline forms of this compound (I) or a pharmacologically acceptable salt thereof are disclosed in Japanese Patent No. 2001-072681, Japanese Patent Application Publication (Kokai) No. 2002-161034, US 2002/0128254, U.S. Pat. No. 6,924,279, US 2003/0232803 and US 2004/0132668. Although said crystalline forms have superior storage stability and easy handling as compared with lyophilized powders, it cannot necessarily be assumed that there is no problem at all with respect to producability and storage stability.

SUMMARY OF THE INVENTION

Therefore, the inventors made many efforts in order to solve these problems and have succeeded in obtaining certain novel crystalline forms of compound (I). The inventors have found that these crystalline forms of compound (I) have superior producability and storage stability compared to the crystalline forms described in the examples of Japanese Patent Application Publication (Kokai) No. 2001-072681, and are extremely useful medicaments, especially, practically useful antibiotic agents, thereby leading to completion of the present invention.

More specifically, the crystalline form (I-1) to be described later can be produced both in high yield and by a simple procedure, does not require special drying conditions in the drying step, and has improved storage stability under dry conditions. The crystalline form (I-2) to be described later can be produced by a simple procedure, does not require a drying step or can be dried in a short period of time, and is handled easily since it is stable during storage under conditions of normal or high humidity. The crystalline form (I-3) to be described later containing a specific amount of water can be produced in high yield and by a simple procedure, does not require a drying step or can be dried in a short period of time, and is handled easily since it is stable during storage under conditions of normal or high humidity.

This invention is directed to the following:

(1) a 1-methylcarbapenem compound ethanolate of the formula (I-1) in the crystalline form that shows main peaks at interplanar spacings d=7.60, 6.69, 6.33, 6.14, 5.15, 4.58 and 4.48 in the X-ray powder diffraction pattern obtained with Cu $K_\alpha$ irradiation

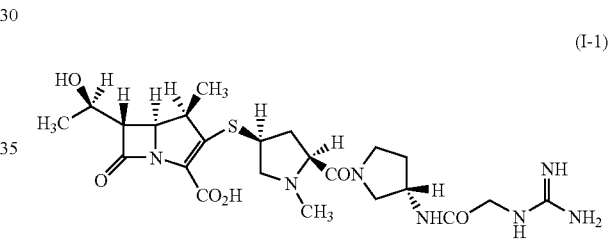

(referred to as crystalline form (I-1));

(2) a 1-methylcarbapenem compound tetrahydrate of the formula (I-2) in the crystalline form that shows main peaks at interplanar spacings d=11.68, 8.79, 7.53, 6.57, 5.58, 5.37, 3.99 and 3.09 in the X-ray powder diffraction pattern obtained with Cu $K_\alpha$ irradiation

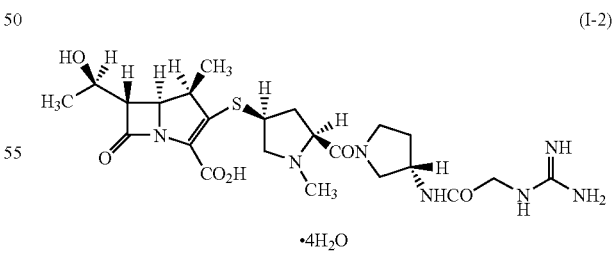

(referred to as crystalline form (I-2));

(3) a process for the preparation of the crystalline form (I-1) comprising drying at normal temperature (such as 10° C. to 60° C., preferably 15° C. to 25° C.) and under reduced pressure a 1-methylcarbapenem compound ethanolate trihydrate of the formula (I-3) in the crystalline form that shows main peaks at interplanar spacings d=6.65, 5.68, 4.86, 4.57 and 4.03 in the X-ray powder diffraction pattern obtained with Cu $K_\alpha$ irradiation (described in Japanese Patent Application Publication (Kokai) No. 2001-7268, hereinafter referred to as crystalline form (I-3));

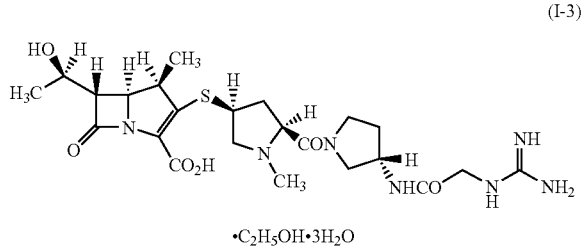

(I-3)

·$C_2H_5OH·3H_2O$ (4) a process for preparation of the crystalline form (I-3) comprising hydrating the crystalline form (I-1);
(5) the crystalline form (I-1) wherein the water content is 0.5 to 2% by weight;
(6) the crystalline form (I-3) wherein the water content is 8 to 10% by weight; and
(7) a solid pharmaceutical composition comprising an above crystalline form of the present invention as an active ingredient, particularly as an antibiotic agent.

The present invention is also directed to a method of preventing or treating a bacterial infection comprising administering to a warm-blooded animal, such as a human, in need thereof, a pharmacologically effective amount of a 1-methylcarbapenem compound ethanolate, a 1-methylcarbapenem compound tetrahydrate or a 1-methylcarbapenem compound ethanolate trihydrate as described above.

In the above description, the 1-methylcarbapenem compound of formula (I) is disclosed in Japanese Patent Application Publication (Kokai) Hei-10-204086 and Hei-11-071277 and exhibits potent antibiotic activity against a wide spectrum of bacterial strains ranging from Gram-positive to Gram-negative bacterial strains.

DETAILED DESCRIPTION OF THE INVENTION

Figure 1:
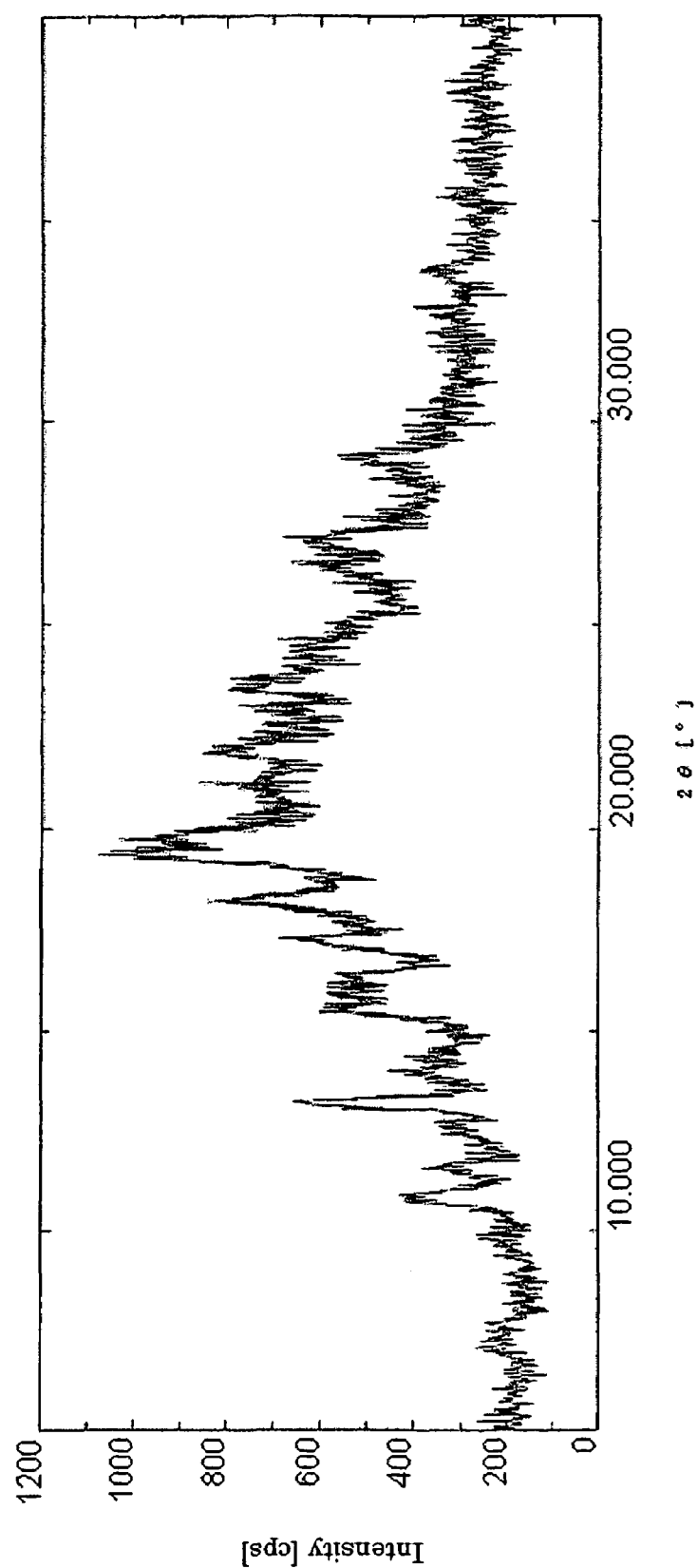
FIG. 1 shows the X-ray powder diffraction pattern of crystalline (1R,5S,6S)-2-[(2S,4S)-2-[(3S)-3-(2-guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid ethanolate (formula (I-1)). The diffraction pattern was obtained with Cu $K_\alpha$ irradiation of $\lambda=1.54$ Å. The vertical axis of the X-ray powder diffraction pattern indicates the diffraction intensity in units of counts/second (cps). The horizontal axis indicates diffraction angle as the value $2\theta$.
Figure 2:
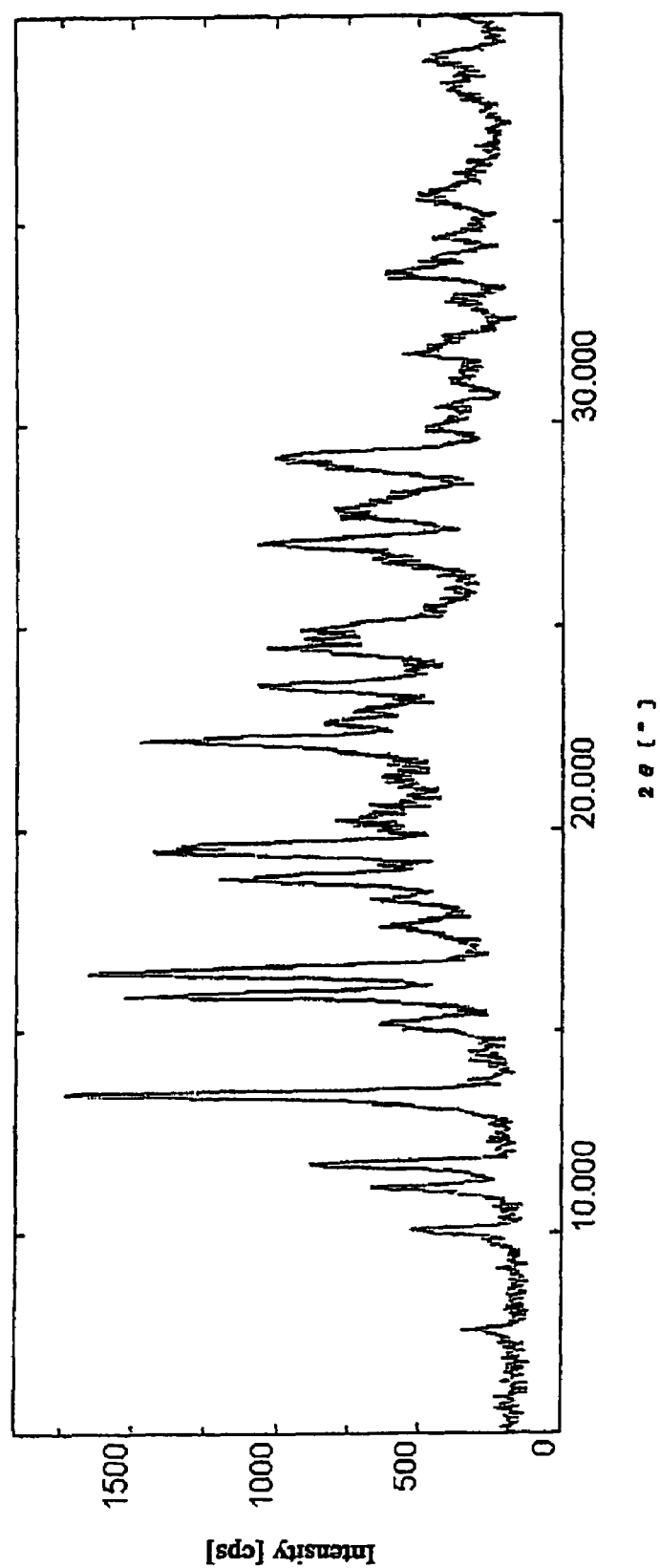
FIG. 2 shows the X-ray powder diffraction pattern of crystalline (1R,5S,6S)-2-[(2S,4S)-2-[(3S)-3-(2-guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid tetrahydrate (formula (I-2)). The diffraction pattern was obtained with Cu $K_\alpha$ irradiation of $\lambda=1.54$ Å. The vertical axis of the X-ray powder diffraction pattern indicates the diffraction intensity in units of counts/second (cps). The horizontal axis indicates diffraction angle as the value $2\theta$.

The compound (I) can exist as pharmacologically acceptable salts. The term "a pharmacologically acceptable salt" as used herein and in the claims is intended to include salts which are usually able to be used as medicaments.

The compound (I) has basic groups such as a tertiary amino group and a guanidino group in its molecule and can be converted to a corresponding pharmacologically acceptable acid addition salt when treated with an appropriate acid employing conventional techniques. Examples of such acid addition salts include inorganic acid salts such as hydrochlorides, hydrobromides, sulfates and phosphates; organic acid salts such as carbonates, acetates, benzoates, oxalates, maleates, fumarates, tartrates and citrates; and sulfonates such as methanesulfonates, benzenesulfonates and p-toluenesulfonates.

The compound (I) has an acidic group such as a carboxyl group in its molecule and can be converted to a corresponding pharmacologically acceptable base addition salt when treated with an appropriate base employing conventional techniques. Examples of such base addition salts include alkali metal salts such as sodium salts, potassium salts and lithium salts; alkaline earth metal salts such as calcium salts and magnesium salts; metal salts such as aluminum salts, iron salts, zinc salts, copper salts, nickel salts and cobalt salts; and quaternary ammonium salts such as ammonium salts.

In addition, when allowed to stand in the air, certain forms of the compound (I) and pharmacologically acceptable salts thereof may absorb or adsorb water and can form hydrates. In certain cases forms of the compound (I) and pharmacologically acceptable salts thereof absorb certain solvents and can form solvates. The compound (I) of this invention and pharmacologically acceptable salts thereof include such hydrates and solvates.

Such salts, hydrates and solvates are preferably sodium salts, hydrochlorides, sulfates, carbonates, hydrates or ethanolates; most preferably carbonates, hydrates or ethanolates.

The compound of formula (I-1) represents the ethanolate of the compound (I). The compound of formula (I-2) represents the tetrahydrate of the compound (I).

The crystalline forms of the present invention are solids which have regular arrangements of atoms (group of atoms) in a three-dimensional structure and repeat the arrangements. The crystals are different from an amorphous solid that has no such regular arrangement of atoms in a three-dimensional structure.

In general, certain compounds produce a plurality of crystalline forms (polymorphic crystals) according to crystallization conditions, crystals of which are different in their three-dimensional arrangement of atoms and in their physicochemical properties. This invention may include each of such crystalline forms and mixtures of two or more thereof.

The crystalline form of the 1-methylcarbapenem compound of formula (I-1) shows main peaks at interplanar spacings d=7.60, 6.69, 6.33, 6.14, 5.15, 4.58 and 4.48 in the X-ray powder diffraction pattern obtained with Cu $K_\alpha$ irradiation of $\lambda=1.54$ Å.

The crystalline form of the 1-methylcarbapenem compound of formula (I-2) shows main peaks at interplanar spacings d=11.68, 8.79, 7.53, 6.57, 5.58, 5.37, 3.99 and 3.09 in the X-ray powder diffraction pattern obtained with Cu $K_\alpha$ irradiation of $\lambda=1.54$ Å.

Among crystalline forms of compound (I) or a pharmacologically acceptable salt thereof, the crystalline forms of the present invention have superior producability and storage stability, and are useful in industrial production.

The 1-methylcarbapenem compound of formula (I) can be prepared by the same technique as described, or by a similar procedure, to that described in Japanese Patent Application Publication (Kokai) Hei-10-204086 and Hei-11-071277.

The crystalline forms of the present invention can be obtained, for example, by dissolving the compound (I) or a pharmacologically acceptable salt thereof in an appropriate solvent which can readily dissolve it, if necessary, concentrating the solution, adding to the solution an appropriate solvent which can slightly dissolve compound (I) or a pharmacologically acceptable salt thereof or cooling the solution in order to lead to a supersaturated solution and hence to crystallization, and isolating the crystals and then drying the crystals.

Precipitation of the crystals can be spontaneous in the vessel, or precipitation can also be initiated or accelerated by addition of crystalline seeds or by mechanical stimulation such as ultrasonic wave irradiation and scratching on the surface of the vessel.

Pharmacologically acceptable salts of compound (I) are preferably hydrochlorides, sulfates or carbonates. The pharmacologically acceptable salts can be prepared by addition of a necessary amount of a desired acid or base to a solution of compound (I).

When solutions of the compound (I) or a pharmacologically acceptable salt thereof are treated, the solutions of these compounds are usually treated at 0° C. to 60° C. in order to avoid decomposition of these compounds; preferably at 0° C. to 25° C.

The preferred temperature for crystallization of these compounds is at 0° C. to 10° C.

Examples of methods of concentration of solutions of the compound (I) or a pharmacologically acceptable salt thereof include an evaporation method using a rotary evaporator under reduced or normal pressure upon heating and a concentration method using a reverse osmotic membrane. The reverse osmotic membrane used in concentration of an aqueous solution can be selected from polyacrylonitrile membranes, polyvinyl alcohol membranes, polyamide membranes and cellulose acetate membranes.

Examples of solvents which can readily dissolve compound (I) or a pharmacologically acceptable salt thereof include water, dimethyl sulfoxide, dimethylformamide and methanol, preferably water.

Examples of solvents which can slightly dissolve compound (I) or a pharmacologically acceptable salt thereof include alcohols having two to four carbon atoms such as ethanol, propanol and butanol; ketones such as acetone and methyl ethyl ketone; ethers such as diethyl ether and tetrahydrofuran; and esters such as methyl acetate and ethyl acetate; preferably ethanol or acetone; most preferably ethanol.

The starting compound (I) which is isolated as a lyophilized powder can be used. A crude preparation containing compound (I) can also be used because it can be purified by crystallization.

Supersaturation can be accomplished, for example, by concentration of an aqueous solution of compound (I) at 30° C. to 60° C. to a saturated aqueous solution, followed by gradually cooling to 0° C. to 10° C. or by gradual addition of an appropriate solvent which can slightly dissolve compound (I) or a pharmacologically acceptable salt thereof, such as ethanol or acetone, to the saturated aqueous solution, if necessary, followed by cooling.

Crystalline forms of this invention are preferably precipitated by concentrating aqueous solutions of compound (I) or a pharmacologically acceptable salt thereof, if necessary, followed by the addition of a solvent which can slightly dissolve these compounds, followed by cooling.

More preferably, crystalline forms of this invention are precipitated by concentrating aqueous solutions of compound (I) or a pharmacologically acceptable salt thereof, if necessary, followed by the addition of ethanol or acetone, and then cooling.

Most preferably, crystalline form (I-1) is precipitated by concentrating aqueous solutions of compound (I) followed by the addition of sodium hydrogencarbonate and ethanol, followed by cooling; and, crystalline form (I-2) is precipitated by cooling aqueous solutions of compound (I), followed by addition of sodium hydrogencarbonate and acetone, followed by cooling, or is precipitated by cooling aqueous solutions of compound (I).

The precipitated crystals can be isolated, for example, by filtration, centrifugation or decantation. If necessary, the isolated crystals can be washed with an appropriate solvent. Preferably the crystals are washed with the solvent used for crystallization.

Isolated crystalline form (I-1) is dried at 10° C. to 50° C., preferably at 20° C. to 30° C. until the weight of the crystalline form becomes constant. If necessary, crystalline form (I-1) may be dried in the presence of drying agents such as silica gel and calcium chloride under reduced pressure.

In the present specification, the terminology of "reduced pressure" includes a preferred pressure of 100 mmHg or less than 100 mmHg and more preferably 20 mmHg or less than 20 mmHg.

Crystalline form (I-2) can be obtained by drying under reduced pressure or by allowing the crystalline form to stand at 10° C. to 60° C., preferably at 20° C. to 30° C., and at a humidity of 30% or more, preferably at a humidity of 70% to 90%, for 30 minutes to 2 days, preferably for 6 hours to 1 day.

Crystalline form (I-1) thus obtained has improved storage stability under dry conditions, and crystalline form (I-2) is handled easily since it is stable during storage under conditions of normal or high humidity.

Crystalline form (I-1) of the present invention can be converted to crystalline form (I-3) described in Japanese Patent Application Publication (Kokai) No. 2001-72681 by humidifying it. In addition, crystalline form (I-3) can be conversely converted to crystalline form (I-1) by drying it.

When crystalline form (I-1) is converted to crystalline form (I-3), the conversion is achieved, for example, by allowing it to stand undisturbed at 10° C. to 60° C., preferably at 20° C. to 30° C., and at a humidity of 30% or more, preferably at a humidity of 50% to 70%, for 30 minutes to 2 days, preferably for 6 hours to 1 day.

When crystalline form (I-3) is converted to crystalline form (I-1), the conversion is achieved, for example, by drying it under reduced pressure at 10° C. to 60° C., preferably at 15° C. to 25° C., for 2 hours to 2 days, preferably for 12 hours to 1 day, or by allowing to stand at 10° C. to 60° C., preferably at 20° C. to 30° C., at a humidity of 20% or less, preferably at a humidity of 10% or less, for 2 hours to 2 days, preferably for 6 hours to 1 day.

As previously described, crystalline form (I-1) and crystalline form (I-3) can have different degrees of water absorption depending on the environment. Even if their degrees of water absorption differ, they are each included in crystalline form (I-1) or crystalline form (I-3) of the present invention provided they demonstrate an X-ray powder diffraction pattern that is the same as that of crystalline form (I-1) or crystalline form (I-3), respectively. Their degrees of water absorption can be measured and determined, for example, according to ordinary methods such as the Karl Fischer method. They can be represented in terms of, for example, their water content. The water content of crystalline form (I-1) is preferably 0.5% to 2%. If the water content is lower than this range, harsh drying conditions may be necessary, resulting in increased production costs. Conversely, if the water content is higher than this range, there may be an increased risk of the crystalline form (I-1) converting to crystalline form (I-3). In addition, the water content of crystalline form (I-3) is preferably 3% to 12%, more preferably 8% to 10%. If the water content is lower than this range, there may be an increased risk of the crystalline form (I-3) converting to crystalline form (I-1). Conversely, if the water content is higher than this range, the crystalline form may be more difficult to handle. In this manner, when crystalline forms (I-1) and (I-3) have their water contents within these ranges, they have particularly superior storage stability, and since there are no fluctuations in quality at normal temperature and normal humidity, they have extremely easy handling properties making them suitable for practical use as a medicament, particularly as an antibiotic agent.

Crystalline form (I-3) having a specific water content as described above can be handled easily, since it remains stable during storage under conditions of normal or high humidity.

The crystalline forms of this invention exhibit a wide spectrum of antibiotic activity and potent antibacterial activities against Gram-positive and Gram-negative strains and anaerobic bacteria, as well as bacteria producing cephalosporinase. When the antibacterial activities of the crystalline forms of this invention were determined by the agar-plate dilution method, they exhibited potent antibacterial activities against various bacteria, for example, Gram-positive strains such as *Staphylococcus aureus*, methicillin-resistant *Staphylococcus aureus*, *Streptococcus pneumoniae*, *Enterococcus* and the like; Gram-negative strains such as *Escherichia coli, Bacillus dysenteriae, Klebsiella pneumoniae, Proteus vulgaris, Serratia, Enterobacteriaceae, Pseudomonas aeruginosa* and the like; and anaerobic bacteria such as *Bacteroides fragilis*. Moreover, the crystalline forms of this invention exhibited potent antibacterial activity against *Helicobacter pylori*, which is often detected in the patients with chronic gastritis and peptic ulcers.

When appropriate solutions of the crystalline forms of this invention were administered to mice, they exhibited long half-value periods of blood concentration and good urinary recovery compared to those of similar compounds known to those skilled in the art.

In addition, when the crystalline forms of this invention were subcutaneously administered to mice infected systemically with *Staphylococcus aureus, Streptococcus pneumoniae, Escherichia coli* or *Pseudomonas aeruginosa*, they exhibited excellent treatment effect. The crystalline forms of this invention, therefore, are useful as medicaments (especially antibacterial agents) as well as bulk powders for the production thereof.

When the crystalline forms of this invention are used as medicaments (especially as antibacterial agents), they can be administered alone or as a mixture of said crystalline forms of this invention and a pharmacologically acceptable carrier(s) such as excipient(s) and diluent(s); they can be administered in various dosage forms such as tablets, capsules, granules, powders or syrups for oral administration, such as injections for parenteral administration or such as ointments for topical application.

Such dosage forms are prepared by methods known to those skilled in the art using additives such as excipients (for example, sugar derivatives such as lactose, sucrose, glucose, mannitol and sorbitol; starch derivatives such as corn starch, potato starch, α-starch, dextrin and carboxymethylstarch; cellulose derivatives such as crystalline cellulose, low-substituted hydroxypropylcellulose, hydroxypropylmethyl cellulose, carboxymethylcellulose, calcium carboxymethyl cellulose and internally-cross-linked sodium carboxymethylcellulose; arabic gum; dextran; pullulan; silicate derivatives such as light anhydrous silicic acid, synthetic aluminum silicate and magnesium metasilicate aluminate; phosphate derivatives such as calcium phosphate; carbonate derivatives such as calcium carbonate; and sulfate derivatives such as calcium sulfate), binders (for example, excipients as described above; gelatin; polyvinylpyrrolidone; and macrogol), disintegrants (for example, excipients as described above, and chemically modified starch and cellulose derivatives such as cross-carmellose sodium, sodium carboxymethylstarch and cross-linked polyvinylpyrrolidone), lubricants (for example, talc; stearic acid; metal stearates such as calcium stearate and magnesium stearate; colloidal silica; bee gum; waxes such as beeswax and spermaceti; boric acid; glycol; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicic acids such as anhydrous silicic acid and silicic acid hydrate; and starch derivatives as described for the excipients), stabilizers (for example, paraoxybenzoic acid esters such as methylparaben and propylparaben; alcohols such as chlorobutanol, benzyl alcohol and phenethyl alcohol; benzalkonium chloride; phenols such as phenol and cresol; thimerosal; acetic anhydride; and sorbic acid), corrigents (for example, sweetening, souring and flavoring agents all of which are usually used), suspending agents (for example, Polysorbate 80 and sodium carboxymethyl cellulose), diluents, solvents for formulation (for example, water, ethanol and glycerin), assisting agents for dissolution (for example, non-ionic surfactants and anionic surfactants), and topical anaesthetic agents (for example, lidocaine hydrochloride and mepivacaine hydrochloride).

Dosage forms for oral administration include, for example, solid dosage forms such as tablets, coated tablets, capsules, troches, powders, fine granules, granules and dry syrups and liquid dosage forms such as syrups. Dosage forms for parenteral administration include, for example, injections, dripping infusions and suppositories. In addition, dosage forms for topical application include, for example, ointments, tinctures, creams and gels. These dosage forms can be prepared using methods known in the field of pharmaceutical technology.

Preferable dosage forms of the crystalline 1-methylcarbapenem compounds of this invention are injections and dripping infusions. Suitable dosage levels for the crystalline forms depend on the age, body weight and symptoms of the patient and are usually from 0.16 mg/kg (preferably 0.83 mg/kg) to 100 mg/kg (preferably 66.7 mg/kg), for example, 10 mg (preferably 50 mg) to 6000 mg (preferably 4000 mg) for an adult human per day, which dosage can be administered as a single dose or divided into 2 to 4 doses throughout the day.

In the present specification, the terminology of "preventing or treating" includes the amelioration or cure of diseases, as well as the suppression of the progress or inhibition of the onset of diseases, and the prevention of recurrence of diseases.

The following examples, test examples and formulation examples further illustrate this invention. Furthermore, all NMR spectra in the examples were determined in deuterated water using tetramethylsilane as internal standard.

EXAMPLE 1

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid ethanolate
(Crystalline form (I-1))

To a solution of (1R,5S,6S)-2-[(2S,4S)-2-[(3S)-3-[2-[2,3-bis(4-nitrobenzyloxycarbonyl)guanidine]acetylamino]-pyrrolidin-1-ylcarbonyl]-1-methylpyrrolidin-4-ylthio]-6-[(1R)-1-hydroxyethyl]-1-methyl-1-carbapen-2-em-3-carboxylic acid 4-nitrobenzyl ester (10.0 g) obtained according to the method described in Japanese Patent Application Publication (Kokai) No. 2001-72681 in tetrahydrofuran (120 mL, which contains water (33%)) was added 7.5% palladium-carbon (3.13 g) and the resulting suspension was stirred under a hydrogen atmosphere at 20° C. for 4 hours. The reaction mixture was then filtered and the filtrate was extracted and washed with ethyl acetate. Activated charcoal (4.3 g) was added to the aqueous layer followed by stirring for 30 minutes at room temperature. After filtering out the activated charcoal, the filtrate was concentrated under reduced pressure. Sodium hydrogencarbonate (100 mg) and ethanol (240 mL) were then added to the resulting concentrate, and the resulting suspension was allowed to stand undisturbed at 0° C. for 16 hours. Subsequently, the suspension was stirred for 1 hour and the precipitated crystals were filtered out and washed with a mixture of ethanol and water (3:1) followed by drying under reduced pressure to obtain crystalline forms of the title ethanolate (4.35 g).

Melting point: 225-240° C. (decomp.)

NMR spectrum (400 MHz, $D_2O$) δ ppm: 1.17-1.94 (6H, m), 1.31 (3H, d, J=6.4 Hz), 1.56-1.74 (1H, m), 1.94-2.12 (1H, m), 2.19-2.29 (1H, m), 2.28, 2.29 (3H, s×2), 2.72-2.88 (2H, m), 3.08 (1H, d, J=10.5 Hz), 3.29-3.74 (8H, m), 3.74-3.94 (2H, m), 4.01 (2H, s), 4.17-4.28 (2H, m), 4.39-4.54 (1H, m).

IR spectrum (KBr) vmax ($cm^{-1}$): 3335, 2970, 1755, 1651, 1452, 1387, 1251.

Powder X-ray (Cu $K_α$, λ=1.54 Å) d (Å): 7.60, 6.69, 6.33, 6.14, 5.15, 4.58, 4.48.

EXAMPLE 2

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid tetrahydrate (Crystalline form (I-2))

To water (14 mL) was added (1R,5S,6S)-2-[(2S,4S)-2-[(3S)-3-(2-guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid (5.50 g) obtained according to the method described in Japanese Patent Application Publication (Kokai) No. 2001-72681 and the resulting suspension was stirred at 0° C. for 1 hour. The resulting crystals were filtered out and dried under reduced pressure to obtain anhydrous crystals. These anhydrous crystals were then allowed to stand undisturbed for one day in an atmosphere at 25° C. and 80% humidity to obtain crystalline forms of the title tetrahydrate (5.28 g).

Melting point: 235-250° C. (decomp.).

NMR spectrum (400 MHz, $D_2O$) δ ppm: 1.34 (3H, dd, J=7.1, 1.9Hz), 1.44 (3H, d, J=6.4 Hz), 1.58-1.68 (1H, m), 1.96-2.13 (1H, m), 2.18-2.34 (1H, m), 2.27, 2.28 (3H, s×2), 2.69-2.89 (2H, m), 3.07 (1H, d, J=10.7Hz), 3.29-3.74 (6H, m), 3.75-3.94 (2H, m), 4.00 (2H, s), 4.16-4.31 (2H, m), 4.37-4.49 (1H, m).

IR spectrum (KBr) vmax ($cm^{-1}$): 3336, 2967, 1753, 1628, 1576, 1451, 1384, 1285, 1182.

Powder X-ray (Cu $K_α$, λ=1.54 Å) d (Å): 11.68, 8.79, 7.53, 6.57, 5.58, 5.37, 3.99, 3.09.

EXAMPLE 3

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid ethanolate (Crystalline form (I-1))

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid ethanolate trihydrate obtained according to the method described in Japanese Patent Application Publication (Kokai) No. 2001-72681 (which is incorrectly described in the aforementioned publication as "½ carbonate ½ ethanol", 4.76 g) was dried under reduced pressure at 20° C. for 6 hours to obtain the title ethanolate (2.55 g).

EXAMPLE 4

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid ethanolate trihydrate (Crystalline form (I-3))

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid ethanolate (42.89 g) obtained in Example 1 was placed in a container at 25° C. and 60% humidity followed by allowing it to stand undisturbed for one day to obtain the title ethanolate trihydrate (45.46 g).

Melting point: 228-233° C. (decomp.).

MNR spectrum (400 MHz, $D_2O$) δ ppm: 1.13-1.24 (4.5H, m), 1.30 (3H, d, J=6.4 Hz), 1.57-1.72 (1H, m), 1.93-2.10 (1H, m), 2.15-2.35 (1H, m), 2.27, 2.29 (3H, s×2), 2.68-2.88 (2H, m), 3.09 (1H, d, J=10.6 Hz), 3.29-3.73 (7H, m), 3.75-3.93 (2H, m), 4.01 (2H, s), 4.12-4.30 (2H, m), 4.38-4.50 (1H, m).

IR spectrum (KBr) vmax ($cm^{-1}$): 3331, 2968, 2875, 2791, 1755, 1669, 1637, 1453, 1386, 1339, 1312, 1283, 1254.

EXAMPLE 5

(1R,5S,6S)-2-[(2S,4S)-2-[(3S)-3-(2-Guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid tetrahydrate (Crystalline form (I-2))

(1R,5S,6S)-2-[(2S,4S)-2-[(3S)-3-[2-[2,3-bis(4-Nitrobenzyloxycarbonyl)guanidino]acetylamino]pyrrolidin-1-ylcarbonyl]-1-methylpyrrolidin-4-ylthio]-6-[(1R)-1-hydroxyethyl]-1-methyl-1-carbapen-2-em-3-carboxylic acid 4-nitrobenzyl ester (3.00 g) obtained according to the method described in Japanese Patent Application Publication (Kokai) No. 2001-72681 was dissolved in tetrahydrofuran (36 mL) containing 33% water followed by the addition of 7.5% palladium-carbon (850 mg) to this solution and stirring the resulting suspension for 4 hours at 20° C. in a hydrogen atmosphere. The reaction mixture was then filtered and the filtrate was extracted and washed with ethyl acetate. Activated charcoal (1.29 g) was added to the resulting aqueous layer followed by stirring for 30 minutes at room temperature. After filtering out the activated charcoal from the reaction liquid, the resulting filtrate was concentrated under reduced pressure. Sodium hydrogencarbonate (30 mg) and acetone (72 mL) were then added to the concentrate, and the suspension was allowed to stand undisturbed for 16 hours at 0° C. Subsequently, the suspension was stirred for 1 hour and the precipitated crystals were filtered out and washed with a mixture of acetone and water (3:1) to obtain crystalline forms of the target tetrahydrate (1.31 g).

The melting point, nuclear magnetic resonance spectrum, infrared absorption spectrum and powder X-ray diffraction results of the resulting crystalline forms were the same as those of the crystalline forms obtained in Example 2.

PREPARATION EXAMPLE 1

Injection Preparation 250 mg of crystalline forms of the compound of Example 1 are aseptically filled and sealed in a vial. Pharmaceutical additives including local anesthetic such as lidocaine hydrochloride can be blended into this preparation as necessary. This preparation is used by dissolving in a solvent such as distilled water for injection at the time of use.

The crystalline forms of the present invention have improved superior producability or storage stability, and are extremely useful in practical terms as a pharmaceutical, and particularly an antimicrobial.

What is claimed is:

1. A 1-methylcarbapenem compound ethanolate of the formula (I-1) in the crystalline form that shows main peaks at interplanar spacings d=7.60, 6.69, 6.33, 6.14, 5.15, 4.58 and 4.48 in the X-ray powder diffraction pattern obtained with Cu $K_\alpha$ irradiation

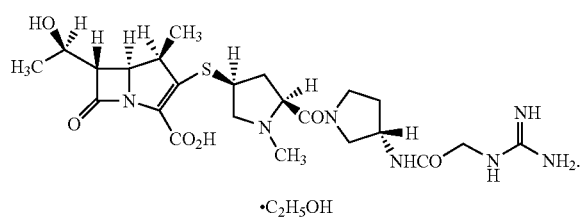

(I-1)

2. The 1-methylcarbapenem compound ethanolate in the crystalline form according to claim 1, which has a water content of 0.5 to 2% by weight.

3. A 1-methylcarbapenem compound tetrahydrate of the formula (I-2) in the crystalline form that shows main peaks at interplanar spacings d=11.68, 8.79, 7.53, 6.57, 5.58, 5.37, 3.99 and 3.09 in the X-ray powder diffraction pattern obtained with Cu $K_\alpha$ irradiation

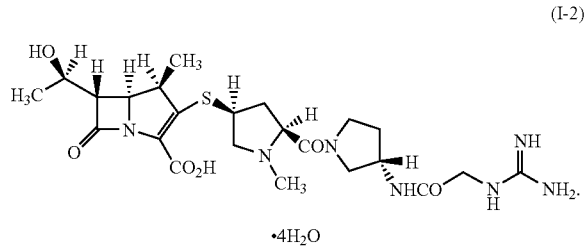

(I-2)

4. A process for the preparation of the 1-methylcarbapenem compound ethanolate in the crystalline form according to claim 1 comprising drying at normal temperature and under reduced pressure a 1-methylcarbepenem compound ethanolate trihydrate of the formula (I-3) in the crystalline form that shows main peaks at interplanar spacings d=6.65, 5.68, 4.86, 4.57 and 4.03 in the X-ray powder diffraction pattern obtained with Cu $K_\alpha$ irradiation

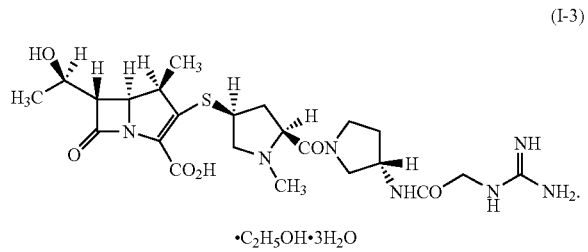

(I-3)

5. A process for preparation of a 1-methylcarbapenem compound ethanolate trihydrate of the formula (I-3) in the crystalline form that shows main peaks at interplanar spacings d=6.65, 5.68, 4.86, 4.57 and 4.03 in the X-ray powder diffraction pattern obtained with Cu $K_\alpha$ irradiation, comprising hydrating the 1-methylcarbapenem compound ethanolate in crystalline form according to claim 1

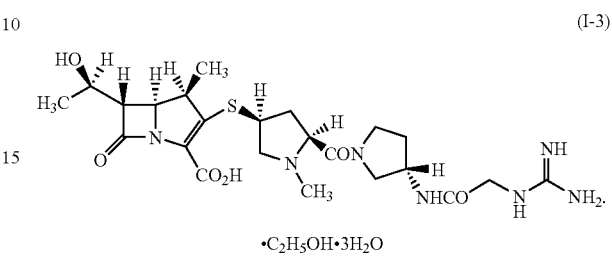

(I-3)

6. A solid pharmaceutical composition for preventing or treating a bacterial infection comprising a pharmacologically effective amount of the 1-methylcarbapenem compound ethanolate in the crystalline form according to claim 1 as an active ingredient, in combination with a pharmaceutically acceptable carrier.

7. A solid pharmaceutical composition for preventing or treating a bacterial infection comprising a pharmacologically effective amount of the 1-methylcarbapenem compound ethanolate in the crystalline form according to claim 2 as an active ingredient, in combination with a pharmaceutically acceptable carrier.

8. A solid pharmaceutical composition for preventing or treating a bacterial infection comprising a pharmacologically effective amount of the 1-methylcarbapenem compound tetrahydrate in the crystalline form according to claim 3 as an active ingredient, in combination with a pharmaceutically acceptable carrier.

9. A method for preventing or treating a bacterial infection comprising administering to a warm-blooded animal in need thereof a pharmacologically effective amount of the 1-methylcarbapenem compound ethanolate in the crystalline form according to claim 1.

10. The method according to claim 9, wherein the warm-blooded animal is a human.

11. The method according to claim 10, wherein the method is for treating a bacterial infection.

12. The method according to claim 11, wherein the bacterial infection is selected from the group consisting of *Staphylococcus aureus*, methicillin-resistant *Staphylococcus aureus*, *Streptococcus pneumoniae*, *Enterococcus*, *Escherichia coli*, *Bacillus dysenteriae*, *Kiebsiella pneumoniae*, *Proteus vulgaris*, *Serratia*, *Enterobacteriaceae*, *Pseudomonas aeruginosa*, *Bacteroides fragilis* and *Helicobacter pylori*.

13. The method according to claim 11, wherein the bacterial infection is selected from the group consisting of *Staphylococcus aureus*, *Streptococcus pneumoniae*, *Escherichia coli* and *Pseudomonas aeruginosa*.

14. A method for preventing or treating a bacterial infection comprising administering to a warm-blooded animal in need thereof a pharmacologically effective amount of the 1-methylcarbapenem compound tetrahydrate in the crystalline form according to claim 3.

15. The method according to claim 14, wherein the warm-blooded animal is a human.

16. The method according to claim 15, wherein the method is for treating a bacterial infection.

17. The method according to claim 16, wherein the bacterial infection is selected from the group consisting of *Staphylococcus aureus*, methicillin-resistant *Staphylococcus aureus, Streptococcus pneumoniae, Enterococcus, Escherichia coli, Bacillus dysenteriae, Kiebsiella pneumoniae, Proteus vulgaris, Serratia, Enterobacteriaceae, Pseudomonas aeruginosa, Bacteroides fragilis* and *Helicobacter pylori*.

18. The method according to claim 16, wherein the bacterial infection is selected from the group consisting of *Staphylococcus aureus, Streptococcus pneumoniae, Escherichia coli* and *Pseudomonas aeruginosa*.

19. A method for preventing or treating a bacterial infection comprising administering to a warm-blooded animal in need thereof a pharmacologically effective amount of the 1-methylcarbapenem compound ethanolate in the crystalline form according to claim 2.

20. The method according to claim 19, wherein the warm-blooded animal is a human.

21. The method according to claim 20, wherein the method is for treating a bacterial infection.

22. The method according to claim 21, wherein the bacterial infection is selected from the group consisting of *Staphylococcus aureus*, methicillin-resistant *Staphylococcus aureus, Streptococcus pneumoniae, Enterococcus, Escherichia coli, Bacillus dysenteriae, Kiebsiella pneumoniae, Proteus vulgaris, Serratia, Enterobacteriaceae, Pseudomonas aeruginosa, Bacteroides fragilis* and *Helicobacter pylori*.

23. The method according to claim 21, wherein the bacterial infection is selected from the group consisting of *Staphylococcus aureus, Streptococcus pneumoniae, Escherichia coli* and *Pseudomonas aeruginosa*.

* * * * *

UNITED STATES PATENT AND TRADEMARK OFFICE
CERTIFICATE OF CORRECTION

PATENT NO. : 7,534,782 B2  
APPLICATION NO. : 11/352825  
DATED : May 19, 2009  
INVENTOR(S) : Michida et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (369) days Delete the phrase "by 369 days" and insert -- by 482 days --

Signed and Sealed this

Twenty-fourth Day of November, 2009

David J. Kappos  
*Director of the United States Patent and Trademark Office*